United States Patent [19]

Meconi et al.

[11] Patent Number: 5,670,164
[45] Date of Patent: Sep. 23, 1997

[54] NITROGLYCERIN-CONTAINING PATCH, A PROCESS FOR THE PRODUCTION AND THE USE THEREOF

[75] Inventors: Reinhold Meconi, Neuwied; Tina Rademacher, Bad Honnef, both of Germany

[73] Assignee: LTS Lohmann Therapie-Systeme BmgH & Co., KG, Neuwied, Germany

[21] Appl. No.: 492,004

[22] PCT Filed: Jan. 10, 1994

[86] PCT No.: PCT/EP94/00053

§ 371 Date: Sep. 29, 1995

§ 102(e) Date: Sep. 29, 1995

[87] PCT Pub. No.: WO94/16691

PCT Pub. Date: Aug. 4, 1994

[30] Foreign Application Priority Data

Jan. 23, 1993 [DE] Germany ............... 43 01 781.9

[51] Int. Cl.$^6$ ................... A61F 13/02
[52] U.S. Cl. ................... 424/448; 424/449
[58] Field of Search ................... 424/448, 449

[56] References Cited

U.S. PATENT DOCUMENTS

| | | | |
|---|---|---|---|
| 3,742,951 | 7/1973 | Zaffaroni | 424/434 |
| 5,273,757 | 12/1993 | Jaeger | 424/448 |
| 5,306,502 | 4/1994 | Jaeger | 424/443 |

FOREIGN PATENT DOCUMENTS

| | | |
|---|---|---|
| 0 175 562 | 3/1986 | European Pat. Off. . |
| 3 222 800 | 1/1983 | Germany . |
| 3 315 272 | 10/1984 | Germany . |
| 3 642 931 | 7/1987 | Germany . |
| 3 743 946 | 3/1989 | Germany . |
| 3 843 239 | 2/1990 | Germany . |

*Primary Examiner*—D. Gabrielle Phelan
*Attorney, Agent, or Firm*—Wenderoth, Lind & Ponack

[57] ABSTRACT

An active substance-containing patch for the controlled release of nitroglycerin to the skin, consisting of an impermeable backing layer, a reservoir attached thereto and comprising pressure-sensitive hot melt adhesive and active substance, and a removable protective layer, in which patch the reservoir comprises in homogeneous mixture:

a) tackifying soft and/or hard resins, b) plasticizers, c) nitroglycerin preparation.

15 Claims, No Drawings

NITROGLYCERIN-CONTAINING PATCH, A PROCESS FOR THE PRODUCTION AND THE USE THEREOF

The present invention relates to an active substance-containing patch for the controlled release of nitroglycerin to the human and animal skin; it has a backing layer which is impermeable to the nitroglycerin and a pressure-sensitive adhesive mono- or multi-layer reservoir comprising nitroglycerin in non-uniform or uniform distribution. The invention further relates to the use of such patches.

Nitroglycerin patches have already been known for some time. The manufacture of nitroglycerin patches is problematic inasmuch as nitroglycerin is explosive and evaporation as well as thermal and mechanical stresses must therefore be avoided to the greatest possible extent.

It is preferable to operate at temperatures which are as low as possible, in particular at room temperature, the nitroglycerin-containing pressure-sensitive adhesive layer frequently being manufactured from a solution. The known patch-like transdermal therapeutic systems for releasing nitroglycerin which are produced in such a manner perform their therapeutic functions, however, production is too expensive.

DE-OS 3222800 (ALZA) describes a nitroglycerin patch using as nitroglycerin-containing matrix a non-adhesive viscous mass obtained by thickening a nitroglycerin solution with a rheological agent at room temperature. Also, U.S. Pat. No. 3,742,951 (CIBA-GEIGY) and DP-PS 3315272 and DE-OS 3315245 (LOHMANN/SCHWARZ) describe nitroglycerin patches of a simple construction having pressure-sensitive adhesive matrix materials which are produced at room temperature from solution.

It is also known to use multi-part nitroglycerin reservoirs, e.g. from DE-OS 3642931 (CIBA-GEIGY).

Pressure-sensitive hot melt adhesives are generally known from EP-A2-175562; however, there is no indication with respect to whether and how these are to be selected for active substance reservoirs, in particular for those containing nitroglycerin.

Generic nitroglycerin patches are described in EP-A 0204968; here a pressure-sensitive adhesive reservoir made of rubber and a tackifying resin is used with nitroglycerin. The pressure-sensitive adhesive reservoir is manufactured from solution, resulting in the problem of withdrawing solvent residues and, in some cases, that of consequently evaporating nitroglycerin.

The use of solvents in the manufacture of the pressure-sensitive adhesive layers is disadvantageous for several reasons. The manufacture of the solutions requires high technical expense since the devices have to be explosion-proof. For medical purposes, absolutely pure and therefore expensive solvents have to be employed to dissolve the adhesives or their starting materials. Another problem is to obtain solvent-free patches, requiring expensive drying and extraction plants. In addition, costs caused by recovery and separation of the solvents to prevent environmental load are involved. Also, the inflammability of the solvents means an additional risk, in particular with the explosive active substance concerned. Furthermore, most organic solvents are harmful to human organisms so that expensive measures must be taken to protect the staff.

A nitroglycerin patch is known from DE-3743946, this is manufactured by coating a nitroglycerin-containing adhesive from a melt at 40°–80° C.

However, in practice the coating involves severe difficulties due to the high viscosity of the coating mass. Owing to the polymeric compounds (e.g. ethylene-vinyl-acetate-copolymers) contained in the nitroglycerin-containing adhesive the viscosity is extremely high so that the manufacture of the nitroglycerin-containing patches is rendered extremely difficult.

Accordingly, it is the object of the present invention to avoid the above disadvantages and to provide a pressure-sensitive hotmelt adhesive allowing perfect processing on a commercial scale.

This object is achieved in that processable melts are obtained by dispensing with polymeric compounds and exclusively using resins.

In this connection, there is a wide scope for formulating the reservoir on the basis of hot melt pressure-sensitive adhesives. For example, the nitroglycerin preparation may be admixed with different soft resins. In addition, different hard resins or the combination of hard and soft resins may be used.

With the present invention, soft resins are tackifying resins which are semisolid or liquid at room temperature or melt up to about 60° C. These include, for example, methyl esters of resin acids, methyl esters of hydrogenated resin acids, triethylene glycol ester of hydrogenated resin acids, hydroabietyl alcohol, phthalic acid esters of hydroabietyl alcohol, aromatic hydrocarbon resins, low-molecular styrene resins, and hydrogenated hydrocarbon resins.

With this invention, hard resins are tackifying resins which are solid at room temperature and soften from about 60° C. These include modified resin acids, hydrogenated and non-hydrogenated resin esters, polymerized resin esters, acid-modified resin esters, aromatic and aliphatic hydrocarbon resins, alpha-methyl-stryrene-resins, alpha-methyl-styrene/vinyl toluene-copolymer-resins, and hydrogenated hydrocarbon resins.

The proportion of tackifying resins in the nitroglycerin-containing adhesive mass amounts to 10–43%-wt.

The nitroglycerin-containing reservoir additionally comprises plasticizers. Suitable plasticizers are known to those skilled in the art and are described, for example, in DE-3743946. The nitroglycerin-containing reservoir normally comprises 0.1–5%-wt. plasticizer.

Usually, anti-ageing agents are also comprised in the active substance-containing reservoir, the concentration amounting to 0.1–2%-wt. These substances are known to those skilled in the art and are described, for example, in DE-3743946.

Also, the materials used for the impermeable backing layer and for the removable protective layer are known to those skilled in the art (e.g. DE-3843239).

A particularly preferred construction of the transdermal nitroglycerin patch is the matrix system, in which, as is generally known, the matrix controls the active substance release which complies with the $\sqrt{t}$-law according to Higuchi. However, this does not mean that the membrane system may be appropriate in particular cases. In this case, a membrane controlling the nitroglycerin release is located between the reservoir and the pressure-sensitive adhesive layer.

In case the reservoir fails to exhibit sufficient self-tackiness to the skin, it may be provided with a pressure-sensitive adhesive layer. This ensures that the transdermal patch adheres to the skin for the whole application period.

The thickness of the transdermal patch depends on the therapeutic requirements and may be adapted accordingly. Usually, it ranges from 0.03–0.4 mm.

In case of insufficient self-tackiness to the skin, another possibility of fixing the reservoir to the skin is to provide it with a pressure-sensitive adhesive edge.

The transdermal patch may be produced in a particularly simple manner. The resins are molten, the other reservoir components are added at a temperature of less than 55° C. and homogenized by kneading or stirring. This results in reservoir masses having a viscosity of 1320–8253 dPa·s. The nitroglycerin-containing reservoir mass so obtained is applied to the removable protective layer, and the impermeable backing layer is laminated.

The machinery necessary for the production of the transdermal patch requires little space and is considerably less expensive than conventional coating machines for processing solvent-containing adhesives. In addition, the machine operates at a high speed amounting to about 10–50 m per minute.

EXAMPLE 1

11.05 g soft resin (hydroabietyl alcohol: trade name Abitol by Hercules), 28.74 g hard resin (aliphatic hydrocarbon resin: Hercures C by Hercules), and 2.29 g plasticizer (medium-chain triglycerides: Miglyol 812 by Dynamit Nobel)

are homogenized by kneading at 120° C. The melt is cooled to 55° C., subsequently 57.47 g nitroglycerin-lactose-preparation (10% nitroglycerin) are added and homogenized by kneading.

The active substance-containing reservoir mass (viscosity: 8253 dPa·s) thus obtained is coated onto the removable protective layer (Hostaphan RN 100; one-side coated with silicone (thickness: 100 μm)—by Kalle) at 55° C. in such a manner that the reservoir has a mass per unit area of 175.5 g/m$^2$. The impermeable backing layer (Hostaphan RN 36 (thickness: 36 μm)—by Kalle) is laminated thereon.

Patches with rounded edges and having a size of 16 cm$^2$ are punched from the laminate thus obtained.

EXAMPLE 2

The manufacture is carried out as in Example 1, however, according to the manufacturing formula given in Table 1; (viscosity: 3301 dPa·s at 55° C.).

EXAMPLE 3

The production is carried out as in Example 1, however, according to the manufacturing formula given in Table 1; (viscosity: 1320 dPa·s at 55° C.).

ANALYTIC PROCEDURE

The active substance release of the transdermal patches of a size of 16 cm$^2$ is determined according to the Rotating bottle-method described in USP XXII in 0.9% solution of sodium chloride at 37° C.

The results are listed in Table 2.

TABLE 1

| | Manufacturing formula | | | | |
|---|---|---|---|---|---|
| Example | Abitol (g) | Hercures C (g) | Miglyol 812 (g) | Nitroglycerin-lactose (10%) (g) | Mass per unit area of reservoir (g/m$^2$) |
| 1 | 11.50 | 28.74 | 2.29 | 57.47 | 175.5 |
| 2 | 16.10 | 24.13 | 2.30 | 57.47 | 172.0 |
| 3 | 20.11 | 20.11 | 2.29 | 57.50 | 175.0 |

TABLE 2

| | Active Substance Release | | | |
|---|---|---|---|---|
| | Active Substance Release (mg nitroglycerin/16 cm$^2$) after | | | |
| Example | 2 hours | 4 hours | 6 hours | 24 hours |
| 1 | 2.15 | 3.88 | 6.08 | 10.87 |
| 2 | 5.50 | 7.19 | 8.60 | 10.26 |
| 3 | 6.85 | 9.76 | 11.71 | 15.67 |

We claim:

1. In an active substance-containing patch for the controlled release of nitroglycerin to the skin, consisting of an impermeable backing layer, a reservoir bonded thereto and comprising pressure-sensitive hot melt adhesive and active substance, and a removable protective layer, the improvement wherein the reservoir consists essentially of a solvent-free homogenized mixture of:

(a) a member selected from the group consisting of (1) a tackifying resin which is semisolid or liquid at room temperature or melts at a temperature up to about 60° C., (2) a tackifying resin which is solid at room temperature and softens at a temperature from about 60° C., and (3) mixtures thereof, (b) a plasticizer, and (c) a nitroglycerin preparation, said mixture being free of other polymers.

2. A patch according to claim 1 wherein component a) is a tackifying resin which is semisolid or liquid at room temperature or melts at a temperature up to about 60° C.

3. A patch according to claim 1 wherein component a) is a tackifying resin which is solid at room temperature and softens at a temperature from about 60° C.

4. A patch according to claim 1 wherein component a) is a mixture of tackifying resins (1) and (2).

5. A patch according to claim 1 wherein the amount of component a) ranges between 10 and 43% by weight.

6. A patch according to claim 1 wherein the reservoir contains 0.3 to 10% by weight nitroglycerin.

7. A patch according to claim 1 wherein the nitroglycerin, in a nitroglycerin-lactose preparation, is mixed into premixed component a) to form the mixture.

8. A patch according to claim 1 wherein the reservoir contains 0.1 to 5% by weight plasticizer.

9. A patch according to claim 1 wherein the reservoir additionally contains 0.1 to 2% by weight anti-aging agent.

10. A patch according to claim 1 wherein the reservoir has a thickness of 0.03 to 0.4 mm.

11. A patch according to claim 1 wherein the reservoir consists of a plurality of layers.

12. A patch according to claim 1, wherein the reservoir is provided with a pressure-sensitive adhesive layer.

13. A patch according to claim 1 wherein the reservoir is provided with a pressure-sensitive adhesive edge.

14. A process for the production of an active substance-containing patch for the controlled release of nitroglycerin to the skin which consists essentially of (a) homogenizing, in a melt by kneading at elevated temperature without the use of solvents, a member selected from the group consisting of (1) a tackifying resin which is semisolid or liquid at room temperature or melts at a temperature up to about 60° C. (2) a tackifying resin which is solid at room temperature and softens at a temperature from about 60° C., and (3) mixtures thereof;

(b) cooling the melt, adding a nitroglycerin preparation thereto and homogenizing by further kneading, (c) coating the thus-obtained active substance-containing reservoir mass onto a removable protective layer at a constant low temperature and laminating an impermeable backing layer thereon, and (d) punching out patches from the thus obtained laminate.

15. A method for the administration of nitroglycerin to a human or an animal which comprises applying to the skin of said human or animal a patch as defined in claim 1.

* * * * *